United States Patent
Huser et al.

(10) Patent No.: US 9,918,861 B2
(45) Date of Patent: *Mar. 20, 2018

(54) PRECANNULATED FENESTRATION

(75) Inventors: Matthew S. Huser, West Lafayette, IN (US); Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1266 days.

This patent is subject to a terminal disclaimer.

(21) Appl. No.: 13/208,793

(22) Filed: Aug. 12, 2011

(65) Prior Publication Data

US 2012/0041535 A1 Feb. 16, 2012

Related U.S. Application Data

(60) Provisional application No. 61/373,610, filed on Aug. 13, 2010.

(51) Int. Cl.
| | |
|---|---|
| *A61F 2/966* | (2013.01) |
| *A61F 2/954* | (2013.01) |
| *A61F 2/07* | (2013.01) |
| *A61F 2/958* | (2013.01) |
| *A61F 2/06* | (2013.01) |
| *A61F 2/95* | (2013.01) |

(52) U.S. Cl.
CPC .............. *A61F 2/966* (2013.01); *A61F 2/954* (2013.01); *A61F 2/07* (2013.01); *A61F 2/958* (2013.01); *A61F 2002/061* (2013.01); *A61F 2002/9511* (2013.01)

(58) Field of Classification Search
CPC .. A61F 2/966; A61F 2/07; A61F 2/954; A61F 2/958

USPC ...... 606/108, 191–200; 623/1.11–1.13, 1.16, 623/1.23, 1.35

See application file for complete search history.

(56) References Cited

U.S. PATENT DOCUMENTS

| | | | |
|---|---|---|---|
| 4,502,159 A | 3/1985 | Woodroof et al. | ................. 3/1.4 |
| 4,675,361 A | 6/1987 | Ward, Jr. | ......................... 525/92 |

(Continued)

FOREIGN PATENT DOCUMENTS

| | | |
|---|---|---|
| CN | 102106767 | 6/2011 |
| EP | 2 417 942 A1 | 2/2012 |

(Continued)

OTHER PUBLICATIONS

European Search Report for corresponding EPO Appln. No. EP 11 27 5106 dated Dec. 14, 2011, 3 pages.

(Continued)

*Primary Examiner* — David C Eastwood
(74) *Attorney, Agent, or Firm* — Brinks Gilson & Lione

(57) ABSTRACT

Devices for delivering and deploying an endoluminal prosthesis are disclosed and comprise a delivery catheter, an endoluminal prosthesis disposed at a distal end portion of the delivery catheter, and a wire. The prosthesis comprises a tubular graft having at least one fenestration. The wire extends distally from a first wire end through an axial lumen of the delivery catheter and the prosthesis, and through the fenestration in the graft. The wire extends proximally through a lumen of the prosthesis and through an axial lumen of the delivery catheter towards a second wire end. Additional devices, systems, and methods are disclosed.

12 Claims, 12 Drawing Sheets

(56) References Cited

U.S. PATENT DOCUMENTS

| | | | |
|---|---|---|---|
| 4,861,830 A | 8/1989 | Ward, Jr. .......................... 525/92 |
| 4,902,508 A | 2/1990 | Badylak et al. ................ 424/95 |
| 5,017,664 A | 5/1991 | Grasel et al. ................... 525/454 |
| 5,380,304 A | 1/1995 | Parker ........................... 604/282 |
| 5,542,434 A | 8/1996 | Imran et al. |
| 5,554,183 A | 9/1996 | Nazari |
| 5,554,389 A | 9/1996 | Badylak et al. |
| 5,628,783 A | 5/1997 | Quiachon et al. |
| 5,702,439 A | 12/1997 | Keith et al. |
| 5,728,122 A | 3/1998 | Leschinsky et al. |
| 5,733,337 A | 3/1998 | Carr, Jr. et al. ................. 623/11 |
| 5,746,766 A | 5/1998 | Edoga ........................... 606/198 |
| 5,800,521 A | 9/1998 | Orth |
| 5,984,955 A | 11/1999 | Wisselink |
| 5,993,844 A | 11/1999 | Abraham et al. |
| 6,099,548 A | 8/2000 | Taheri |
| 6,099,567 A | 8/2000 | Badylak et al. |
| 6,206,931 B1 | 3/2001 | Cook et al. ................. 623/23.75 |
| 6,290,666 B1 | 9/2001 | Devonec |
| 6,325,819 B1 | 12/2001 | Pavcnik et al. |
| 6,358,284 B1 | 3/2002 | Fearnot et al. ............ 623/23.72 |
| 6,379,710 B1 | 4/2002 | Badylak ........................ 424/553 |
| 6,416,499 B2 | 7/2002 | Paul, Jr. ........................ 604/256 |
| 6,485,515 B2 | 11/2002 | Strecker |
| 6,524,335 B1 | 2/2003 | Hartley et al. ................ 623/1.13 |
| 6,533,782 B2 | 3/2003 | Howell et al. |
| 6,589,227 B2 | 7/2003 | Sønderskov Klint ......... 604/524 |
| 6,666,892 B2 | 12/2003 | Hiles et al. ................. 623/23.72 |
| 6,752,826 B2 | 6/2004 | Holloway et al. ........... 623/1.13 |
| 6,939,377 B2 | 9/2005 | Jayaraman et al. ......... 623/1.46 |
| 7,025,758 B2 | 4/2006 | Klint ............................. 604/524 |
| 7,105,020 B2 | 9/2006 | Greenberg et al. |
| 7,172,580 B2 | 2/2007 | Hruska et al. |
| 7,335,224 B2 | 2/2008 | Øhlenschlæger ............ 623/1.11 |
| 7,407,509 B2 | 8/2008 | Greenberg et al. |
| 7,435,253 B1 | 10/2008 | Hartley et al. ................ 623/1.12 |
| 7,537,606 B2 | 5/2009 | Hartley et al. |
| 7,591,843 B1* | 9/2009 | Escano et al. ............... 623/1.11 |
| 7,611,529 B2 | 11/2009 | Greenberg et al. |
| 7,637,920 B2 | 12/2009 | von Lehe et al. |
| 7,651,519 B2 | 1/2010 | Dittman ....................... 623/1.11 |
| 7,674,239 B2 | 3/2010 | Sisken et al. ................... 604/19 |
| 7,722,657 B2 | 5/2010 | Hartley ........................ 623/1.13 |
| 7,828,837 B2 | 11/2010 | Khoury |
| 7,867,270 B2 | 1/2011 | Hartley et al. |
| 7,976,575 B2 | 7/2011 | Hartley |
| 8,034,094 B2 | 10/2011 | Aoba et al. |
| 8,043,354 B2 | 10/2011 | Greenberg et al. .......... 623/1.12 |
| 8,292,951 B2 | 10/2012 | Muzslay |
| 8,709,061 B2 | 4/2014 | Greenberg et al. |
| 8,974,518 B2 | 3/2015 | Bruszewski et al. |
| 9,149,382 B2 | 10/2015 | Greenberg et al. |
| 2001/0034514 A1 | 10/2001 | Parker ........................... 604/525 |
| 2002/0007208 A1* | 1/2002 | Strecker ....................... 623/1.12 |
| 2002/0187288 A1 | 12/2002 | Lim et al. ..................... 428/35.2 |
| 2003/0050684 A1 | 3/2003 | Abrams et al. |
| 2003/0149471 A1 | 8/2003 | Briana et al. ................ 623/1.13 |
| 2004/0106974 A1 | 3/2004 | Greenberg et al. |
| 2004/0116996 A1 | 6/2004 | Freitag |
| 2004/0230287 A1* | 11/2004 | Hartley et al. ................ 623/1.12 |
| 2006/0095118 A1 | 5/2006 | Hartley |
| 2006/0184228 A1 | 8/2006 | Khoury |
| 2006/0229707 A1 | 10/2006 | Khoury |
| 2007/0043425 A1 | 2/2007 | Hartley et al. ................ 623/1.12 |
| 2007/0078395 A1 | 4/2007 | Valaie ...................... 604/164.01 |
| 2007/0100427 A1 | 5/2007 | Perouse |
| 2007/0233223 A1 | 10/2007 | Styrc |
| 2007/0244547 A1 | 10/2007 | Greenan |
| 2007/0299499 A1* | 12/2007 | Hartley et al. ................ 623/1.11 |
| 2008/0262596 A1 | 10/2008 | Xiao |
| 2008/0294234 A1 | 11/2008 | Hartley et al. ................ 623/1.12 |
| 2009/0043377 A1 | 2/2009 | Greenberg et al. |
| 2009/0099640 A1* | 4/2009 | Weng ........................... 623/1.11 |
| 2009/0171451 A1 | 7/2009 | Kuppurathanam et al. |
| 2009/0216308 A1* | 8/2009 | Hartley ........................ 623/1.11 |
| 2009/0312829 A1* | 12/2009 | Aoba et al. ................... 623/1.11 |
| 2010/0057077 A1 | 3/2010 | Ducharme |
| 2010/0262217 A1 | 10/2010 | Bruszewski |
| 2010/0280592 A1 | 11/2010 | Shin et al. |
| 2011/0040366 A1 | 2/2011 | Goetz et al. |
| 2011/0270385 A1* | 11/2011 | Muzslay ....................... 623/1.35 |
| 2011/0307048 A1* | 12/2011 | Ivancev et al. .............. 623/1.11 |
| 2012/0010696 A1 | 1/2012 | Greenberg et al. |
| 2012/0041535 A1 | 2/2012 | Huser et al. |
| 2012/0046728 A1 | 2/2012 | Huser et al. |
| 2013/0046371 A1 | 2/2013 | Greenberg et al. |
| 2013/0245743 A1 | 9/2013 | Norris |
| 2014/0257453 A1 | 9/2014 | Roeder |
| 2015/0073535 A1 | 1/2015 | Aoba et al. |
| 2015/0082585 A1 | 3/2015 | King |

FOREIGN PATENT DOCUMENTS

| | | |
|---|---|---|
| EP | 2 517 671 A2 | 10/2012 |
| IE | 20000744 A1 | 5/2001 |
| JP | 2009-538698 A | 11/2009 |
| JP | 2012-040378 A | 3/2012 |
| JP | 2012-040394 A | 3/2012 |
| JP | 2012-525227 A | 10/2012 |
| WO | WO 9822158 A2 | 8/1997 |
| WO | WO 1998/53761 A1 | 12/1998 |
| WO | WO 2007/142962 A2 | 12/2007 |
| WO | WO 2010/127040 A1 | 4/2010 |
| WO | WO 2011/116308 A1 | 9/2011 |
| WO | WO 2011/136931 A1 | 11/2011 |

OTHER PUBLICATIONS

Office Action and English translation for corresponding Chinese Patent Application No. 201310692534.0 dated Jun. 1, 2015, 15 pages.

Office Action and English translation for corresponding Chinese Patent Application No. 201310692534.0 dated Jan. 20, 2016, 10 pages.

Office Action and English translation for corresponding Chinese Patent Application No. 201310692534.0 dated Jul. 13, 2016, 6 pages.

Partial European Search Report for European Application No. EP 15186703.3 dated Jan. 7, 2016, 6 pages.

European Search Report for European Application No. EP 15186703.3 dated Apr. 6, 2016, 11 pages.

Examination Report for European Application No. EP 15186703.3 dated Nov. 25, 2016, 5 pages.

European Search Report for European Application No. EP 15186703.3 dated Jan. 19, 2017, 4 pages.

Extended European Search Report for EP 17160183.4 dated Jun. 20, 2017, 6 pages.

Office Action and English translation for JP 2015-222071 dated Sep. 27, 2016, 8 pages.

Office Action and English translation for JP 2016-081840 dated Apr. 4, 2017, 8 pages.

Extended European Search Report, European Application No. EP 12197881.1, dated Apr. 2, 2013, European Patent Office, The Netherlands. (pp. 1-5).

Extended European Search Report for European Application No. EP 13197520 dated Apr. 24, 2014, 6 pages.

"Simplified Method of Introducing Double-J Stent Catheters Using a Coaxial Sheath System," Mercado et al., http://www.ajronline.org/doi/pdf/10.2214/ajr.145.6.1271, American Roentgen Ray Society; Dec. 1985 (pp. 1271-1273).

Notice of Allowance from corresponding application U.S. Appl. No. 13/718,915, dated Apr. 8, 2015, 10 pgs.

Notice of Allowance from correspondingapplication U.S. Appl. No. 14/807,333, dated Aug. 28, 2017, 11 pgs.

Extended European Search Report for European Application No. EP 13197520 dated Apr. 21, 2014, 6 pages.

* cited by examiner

PRECANNULATED FENESTRATION

CROSS-REFERENCE TO RELATED APPLICATIONS

This application claims the benefit of the filing date under 35 U.S.C. § 119(e) of U.S. Provisional Patent Application Ser. No. 61/373,610, filed Aug. 13, 2010, which is hereby incorporated by reference.

BACKGROUND OF THE INVENTION

1. Field of the Invention

The present invention relates generally to medical treatment and, in particular, to devices, systems, and methods for delivering and deploying endoluminal medical devices.

2. Description of Related Art

The deployment of a medical device, such as an endoluminal prosthesis, into the vessel of a patient from a remote location by the use of a catheter delivery device is generally known. A catheter delivery device carrying an endoluminal prosthesis is delivered into a vessel over a guide wire previously placed within the vessel. Once the catheter device is positioned, the prosthesis is released and expanded to repair the vessel.

An endoluminal prosthesis can be used, for example, to repair diseased and/or damaged conduits, such as blood vessels, the esophagus, the trachea, and the like. Over the past decade, endoluminal prostheses have become a popular option for treating damage and disease to blood vessels, such as abdominal aortic and/or thoracic aneurysms.

In some cases, it may be necessary to deploy an endoluminal prosthesis in a major vessel (e.g., the aorta) at or near an intersecting branch vessel (e.g., innominate, carotid, subclavian, celiac, SMA, and renal arteries). In these cases, an endoluminal prosthesis may be provided with one or more fenestrations so that the prosthesis can overlap the branch vessels without blocking flow to these vessels. Once the prosthesis is placed in the main vessel, it may be necessary to provide interventional access between the main vessel and a branch vessel. For example, a physician may desire to deliver additional interventional catheters carrying balloons, stents, grafts, imaging devices, and the like through the fenestration.

Before such a catheter device can be delivered through the fenestration to a target vessel, however, a guide wire must be provided and delivered through the fenestration to the target vessel. Typically, this requires multiple steps. First, the physician must deliver and navigate a set of catheters and wires to pass a guide wire through the fenestration. Once the fenestration is cannulated, the physician must then deliver and navigate a separate set of catheters and wires to pass a guide wire into the target vessel. These procedures are labor intensive, involve manipulating multiple wires in a vessel at the same time, and depend heavily on the skill of the physician to cannulate both the fenestration and the target vessel. The steps become even more complicated and numerous when the physician needs to cannulate more than one fenestration and more than one target vessel. In addition, the complexity of the procedure increases as the number of cannulating wires increases, since the physician must take precaution to ensure that the multiple wire ends do not become entangled, or that they do not inadvertently contact and damage the prosthesis or a vessel wall.

The present invention is directed to devices and systems that overcome these, and other issues involved with cannulating fenestrated devices. In particular, the present invention is directed to devices, systems, and methods for delivering and deploying a prosthesis comprising a fenestration, where such devices, systems, and methods include a precannulated fenestration. The precannulated fenestration reduces the potential number of steps and devices, and decreases the complexity of performing endoluminal procedures involving fenestrated prosthetic devices.

SUMMARY

Devices for delivering and deploying an endoluminal prosthesis are described and comprise a delivery catheter having at least one axial lumen, an endoluminal prosthesis disposed at a distal end portion of the delivery catheter, and a wire. The endoluminal prosthesis comprises a tubular graft having a first opening at a first end, a second opening at a second end, and at least one fenestration in the graft between the first and second ends. The wire comprises first and second ends, and a body portion disposed between the first and second ends. The first and second wire ends are each disposed at a proximal end portion of the delivery catheter. The wire extends distally from the first wire end through an axial lumen of the delivery catheter and the prosthesis, and through the fenestration in the graft. The wire also extends proximally through a lumen of the prosthesis and through an axial lumen of the delivery catheter towards the second wire end. The wire provides a precannulating structure for the fenestration, thereby reducing the number of steps and complexity involved in cannulating a target vessel through the fenestration. The provision of both wire ends at the proximal end of the delivery device, away from the prosthesis and the vessel, further reduces potential wire entanglement or damage concerns described above.

In some examples, the wire is slidably disposed through the fenestration. In some examples, the delivery and deployment device comprises an auxiliary catheter slidably disposed within an axial lumen of the delivery catheter over a first end portion of the wire. In addition, a second auxiliary catheter may be provided and slidably disposed within an axial lumen of the delivery catheter over a second end portion of the wire. Each auxiliary catheter may comprise, for example, an elongate sheath and an elongate dilator disposed within an axial lumen of the sheath. One or more attachment points, such as sutures, may be provided between the prosthesis and the wire.

Other devices for delivering and deploying an endoluminal prosthesis are described and comprise a delivery catheter, an endoluminal prosthesis disposed at a distal end portion of the delivery catheter, and a wire. The prosthesis comprises a tubular graft having a first opening at a first end, a second opening at a second end, and at least a first fenestration and a second fenestration in the graft between the first and second ends. The wire comprises first and second ends and a body portion disposed between the first and second ends. Each of the wire ends is disposed at a proximal end portion of the delivery catheter. The body portion of the wire passes through the first fenestration and through the second fenestration in the graft. In some preferred examples, the wire is slidably disposed through the fenestration. The wire provides a precannulating structure for both the first and second fenestrations, thereby reducing the number of steps and complexity involved in cannulating multiple target vessels through the fenestrations.

In some examples, the wire may be disposed, in part, within an axial lumen of the delivery catheter. A delivery and deployment device may comprise a first auxiliary catheter disposed over a first end portion of the wire and a second auxiliary catheter disposed over a second end portion of the wire. One or both of the auxiliary catheters may be slidably disposed within an axial lumen of the delivery catheter. In some examples, a first auxiliary catheter is provided and is slidably disposed within a first axial lumen of the delivery catheter and a second auxiliary catheter is provided and is slidably disposed within a second axial lumen of the delivery catheter. As described above, one or both of the first and second auxiliary catheters may comprise, for example, an elongate sheath and an elongate dilator disposed within an axial lumen of the sheath.

A method of cannulating multiple fenestrations in an endoluminal prosthesis comprises the steps of providing a delivery catheter, disposing an endoluminal prosthesis at a distal end portion of the delivery catheter, and providing a wire having a first end, a second end, and a body portion disposed between the first and second ends. The endoluminal prosthesis comprises a tubular graft having a first opening at a first end, a second opening at a second end, and first and second fenestrations in the graft between the first and second ends. The method further comprises the steps of disposing the body portion of the wire so that it passes through the first fenestration and through the second fenestration, and disposing the first and second ends of the wire at a proximal end portion of the delivery catheter.

DETAILED DESCRIPTION OF THE PREFERRED EMBODIMENTS

Figure 1:
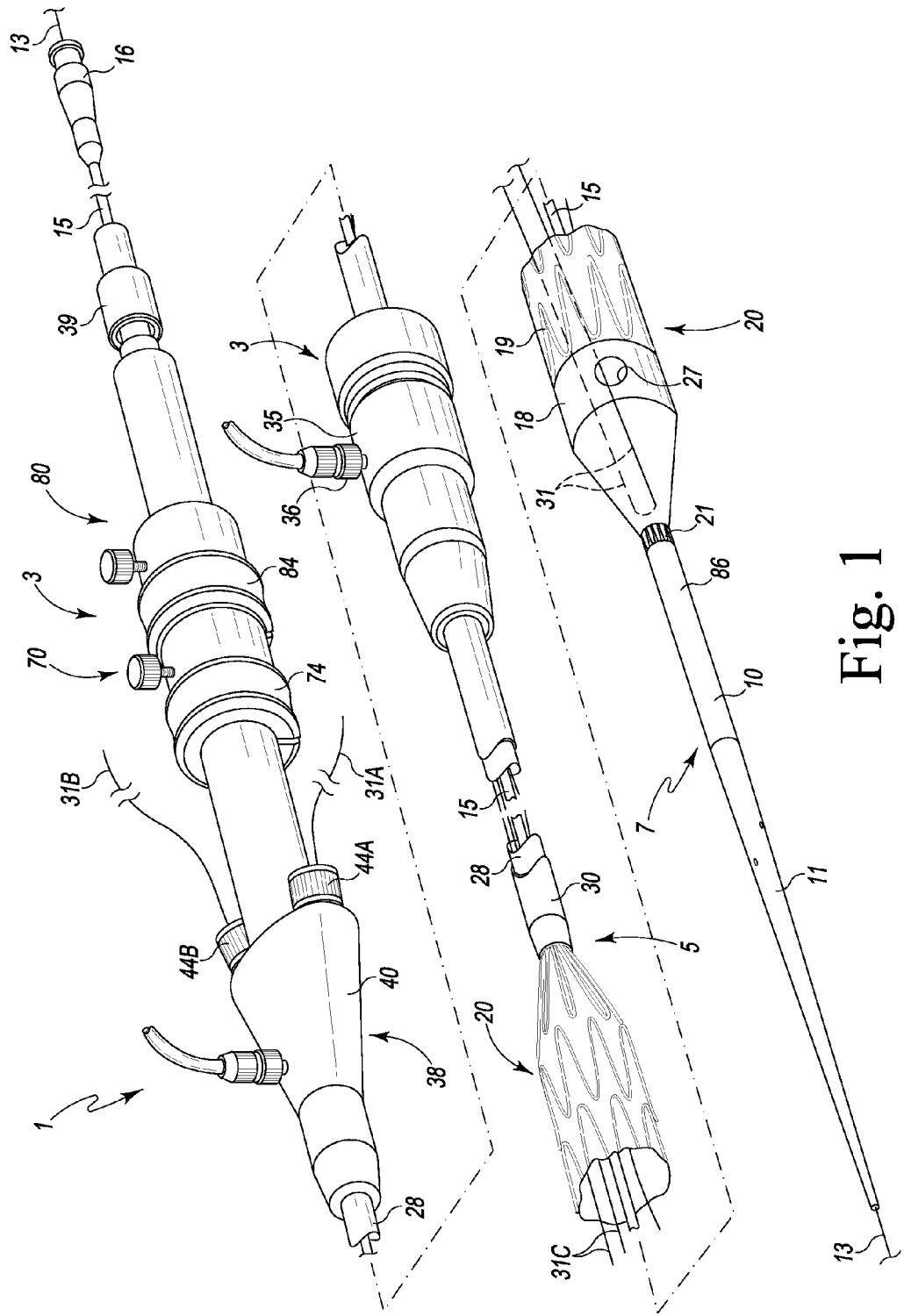
FIG. 1 depicts a device for delivering and deploying an endoluminal prosthesis.

Throughout the specification, when referring to any portion of a device or system for delivering an endoluminal prosthesis, the terms "proximal" and "proximally" shall denote a position, direction, or orientation that is generally toward, or in the direction of, the operator of the device or system. The terms "distal" and "distally" shall denote a position, direction, or orientation that is generally toward, or in the direction of, the patient.

Throughout the specification, unless the context requires otherwise, the words "comprise," "include," "and have," and variations such as "comprising," "including," and "having," imply the inclusion of an item or group of items, without the exclusion of any other item or group of items.

The term "prosthesis" means any device, object, or structure that supports, repairs, or replaces, or is configured to support, repair, or replace a body part or a function of that body part. It can also mean a device that enhances or adds functionality to a physiological system.

The term "stent" means any device or structure that provides or is configured to provide rigidity, expansion force, or support to a body part, for example, a diseased, damaged, or otherwise compromised body lumen. A stent may comprise any suitable biocompatible material, including, but not limited to fabrics, metals, plastics, and the like. Examples of suitable materials include metals such as stainless steel and nitinol, and plastics such as polyethylene terephthalate ("PET"), polytetrafluoroethylene ("PTFE") and polyurethane.

A stent may be "expandable," that is, it may be capable of being expanded to a larger-dimension configuration. A stent may expand by virtue of its own resilience (i.e., self-expanding), upon the application of an external force (i.e., balloon-expandable), or by a combination of both. In one example, a stent may have one or more self-expanding portions and one or more balloon-expandable portions. An example of a suitable self-expanding stent includes Z-STENTS®, which are available from Cook Inc., Bloomington, Ind., USA.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. A stent may be attached to or associated with a graft to form a "stent graft."

A graft material may comprise a biocompatible synthetic or biological material. Examples of suitable synthetic materials include fabrics, woven and non-woven materials, and porous and non-porous sheet materials. One exemplary synthetic graft material includes a woven polyester having a twill weave and a porosity of about 350 ml/min/cm$^2$, and is available from VASCUTEK® Ltd., Renfrewshire, Scotland, UK. Other synthetic graft materials include biocompatible materials such as polyester, polytetrafluoroethylene (PTFE), polyurethane, and the like. Examples of suitable biological materials include, for example, pericardial tissue and extracellular matrix materials such as SIS.

Examples of suitable graft materials are described in U.S. Pat. Nos. 4,502,159, 4,675,361, 4,861,830, 4,902,508, 5,017,664, 5,733,337, 6,206,931, 6,358,284, 6,379,710, 6,666,892, 6,752,826, and 6,939,377, in U.S. Patent Application Publication Nos. 2002/0187288 A1 and 2003/0149471 A1, and in PCT Published Patent Application No. WO 98/22158, which are each incorporated by reference herein in their entirety.

The term "vessel" refers to a tube, cavity, duct, or canal in which fluid may be contained and conveyed or circulated. A body vessel (as opposed to a prosthetic vessel) is a vessel that exists naturally, or is formed naturally in the body. Examples of body vessels include, but are not limited to, blood vessels such as the aorta and the femoral artery, the esophagus, the trachea, the ureter, the bile duct, and the like. Examples of prosthetic vessels include, but are not limited to, stents, grafts, stent grafts, venous or aortal valves, vena cava filters, and the like.

The term "lumen" describes a space within a vessel in which fluid may be contained, conveyed, and/or circulated. The term "endoluminal" means within a lumen, and can refer to objects that are found or that can be placed within a lumen, or methods or processes that occur within a lumen. An "endoluminal prosthesis" is a prosthesis that is found or that can be placed within a lumen. Examples of endoluminal prostheses include, but are not limited to, stents, grafts, stent grafts, venous or aortal valves, vena cava filters, and the like. An endoluminal prosthesis may be generally tubular and comprise one or more lumens. Examples of tubular prostheses include, but are not limited to, straight, curved, branched, and bifurcated prostheses.

FIG. 1 shows a device for delivering and deploying an endoluminal prosthesis 20 in a vessel of a patient. The device includes a delivery catheter 1 comprising an external manipulation section 3, a proximal positioning mechanism or attachment region 5, and a distal positioning mechanism or attachment region 7. The proximal and distal attachment regions 5, 7 are positioned inside the patient's body during a medical procedure, whereas the external manipulation section 3 is positioned outside the patient's body. During a procedure, the operator controls or manipulates the external manipulation section 3 to position the proximal and distal attachment regions 5, 7 and to release the prosthesis 20 into the vessel.

The delivery and deployment device includes an endoluminal prosthesis 20 disposed at a distal end portion of the delivery catheter 1 between the proximal and distal attachment regions 5, 7. The prosthesis 20 may comprise a tubular graft material 18, as described above. The prosthesis 20 may additionally or alternatively comprise one or more expandable stents 19 disposed at least partly coextensive with the graft material 18. Each stent 19 may be coupled to an interior and/or exterior surface of the graft material 18. The prosthesis 20 shown in FIG. 1 comprises a graft material 18 and a plurality of expandable stents 19 disposed coextensive with the graft material 18. In addition, the prosthesis 20 shown in FIG. 1 includes a stent 21 extending from the distal end of the graft material 18 so that it is at least partially uncovered from the graft material 18. The bare stent 21 expands and engages the body lumen, thereby anchoring the prosthesis 20 and preventing the prosthesis from moving after implantation. The stent 21 may comprise anchoring means, for example barbs (not shown) that are configured to grasp the walls of the body lumen.

The prosthesis 20 shown in FIG. 1 further comprises a fenestration 27 disposed in the graft material between proximal and distal end openings of the tubular graft 18. The fenestration 27 provides a fluid pathway through the side wall of the graft tube and allows the prosthesis 20 to be placed in a main vessel in overlapping relationship with an intersecting branch vessel, without interrupting flow to the branch vessel.

The prosthesis 20 is disposed at a distal end portion of the delivery catheter 1. Prosthesis 20 is retained over the delivery catheter 1 by an elongate sheath 30. Sheath 30 comprises an elongate tubular body having an axial lumen (not shown). The sheath 30 extends proximally to the manipulation region 3. The prosthesis 20 is disposed within an axial lumen of the sheath 30 in a radially-compressed configuration. In FIG. 1, the prosthesis 20 is depicted in a partially deployed state, whereby the sheath 30 is partially retracted over the prosthesis, exposing the prosthesis and allowing it to radially expand.

The sheath 30 preferably comprises a flexible structure that is able to bend and flex to negotiate complex and tortuous inner body lumina. The sheath 30 may comprise a biocompatible plastic such as PTFE, polyethylene, nylon, or the like. Examples of suitable sheath devices and materials are disclosed in U.S. Pat. Nos. 5,380,304, 6,589,227, and 7,025,758, and in U.S. Patent Application Publication Nos. 2001/0034514, 2002/0032408, and 2006/01555302, which are incorporated herein by reference in their entirety.

The delivery catheter shown in FIG. 1 further comprises an inner cannula 15 that extends distally from the manipulation region 3 to the distal attachment region 7. The inner cannula 15 has an axial lumen that is configured to receive a guide wire 13. The inner cannula 15 extends distally from a proximal end portion of the delivery catheter 1 to a distal end portion of the catheter. A tapered extension 11 is coupled to the distal end of the cannula 15 and forms the distal end of the delivery catheter 1. Connection means 16 is coupled to the proximal end of the cannula 15. Connection means 16 is adapted to accept a syringe and may be used to introduce reagents into the body lumen.

Cannula 15 is slidingly disposed within the lumen of the sheath 30. The prosthesis 20 is retained over a distal portion of the cannula 15 by the sheath 30. The cannula 15 is preferably flexible so that the device can be advanced within a relatively tortuous vessel, such as a femoral artery or the aortic arch. The cannula 15 may comprise metal, for example aluminum, stainless steel, or nitinol. The cannula 15 is in mechanical communication with the flexible extension 11. This allows the operator to control the flexible extension 11 remotely during a procedure. For example, the operator can rotate or slide the flexible extension 11 relative to the prosthesis 20 by manipulating the cannula 15.

The delivery catheter 1 shown in FIG. 1 further comprises an elongate tubular pusher 28 that extends distally from the manipulation region 3 to the proximal attachment region 5. The cannula 15 is slidably disposed within an axial lumen (not shown) of the pusher 28. The sheath 30 is slidably disposed over a distal end portion of the pusher 28. The pusher 28 may comprise any suitable biocompatible material including metal or plastic. The pusher 28 may comprise a radiopaque material. Suitable materials include, but are not limited to aluminum, nitinol, nylon, polypropylene, and polyethylene. The pusher 28 preferably has high longitudinal column strength to ensure adequate energy transfer between the user and the prosthesis during deployment.

The delivery and deployment device further comprises haemostatic sealing means 35 for controlling blood loss through the delivery and deployment device. The sealing means 35 is fixedly connected to the sheath 30 and couples the sheath and the pusher 28. The sealing means 35 comprises one or more haemostatic valves (not shown) that provide a haemostatic seal between the sheath 30 and the pusher 28. Suitable haemostatic valves include, for example, disk valves, iris valves, and the like. The haemostatic sealing means 35 may also include a side tube 36 that facilitates the introduction of medical reagents between the pusher 28 and the sheath 30. U.S. Pat. Nos. 6,416,499 and 7,651,519, and U.S. Patent Application Publication Nos. 2005/0171479 A1 and 2007/0078395 A1 describe examples of suitable haemostatic sealing devices that can be used with a delivery catheter described in the present application. Each of these patent references is incorporated by reference herein in its entirety.

The distal end of the pusher 28 is disposed adjacent the proximal end of the prosthesis 20. To deploy the prosthesis 20, the operator slides the sheath 30 proximally while applying distal pressure to the pusher 28 in the user manipulation region 3. The pusher prevents the prosthesis 20 from sliding proximally with the sheath 30 when the sheath is withdrawn. As a result, the sheath 30 retracts proximally over the prosthesis 20, exposing the prosthesis, thereby allowing it to expand radially outwardly.

The proximal end of the pusher 28 is connected to an auxiliary access device 38. The access device 38 comprises a housing 40, a channel 42 extending generally axially through the housing, and a port 44 coupled to the channel 42. The port 44 provides fluid and mechanical communication between the user manipulation section 3 and the channel 42, which provides fluid and mechanical communication with an axial lumen 33 of the pusher 28 which, in turn, provides fluid and mechanical communication with the prosthesis 20.

Figure 3:
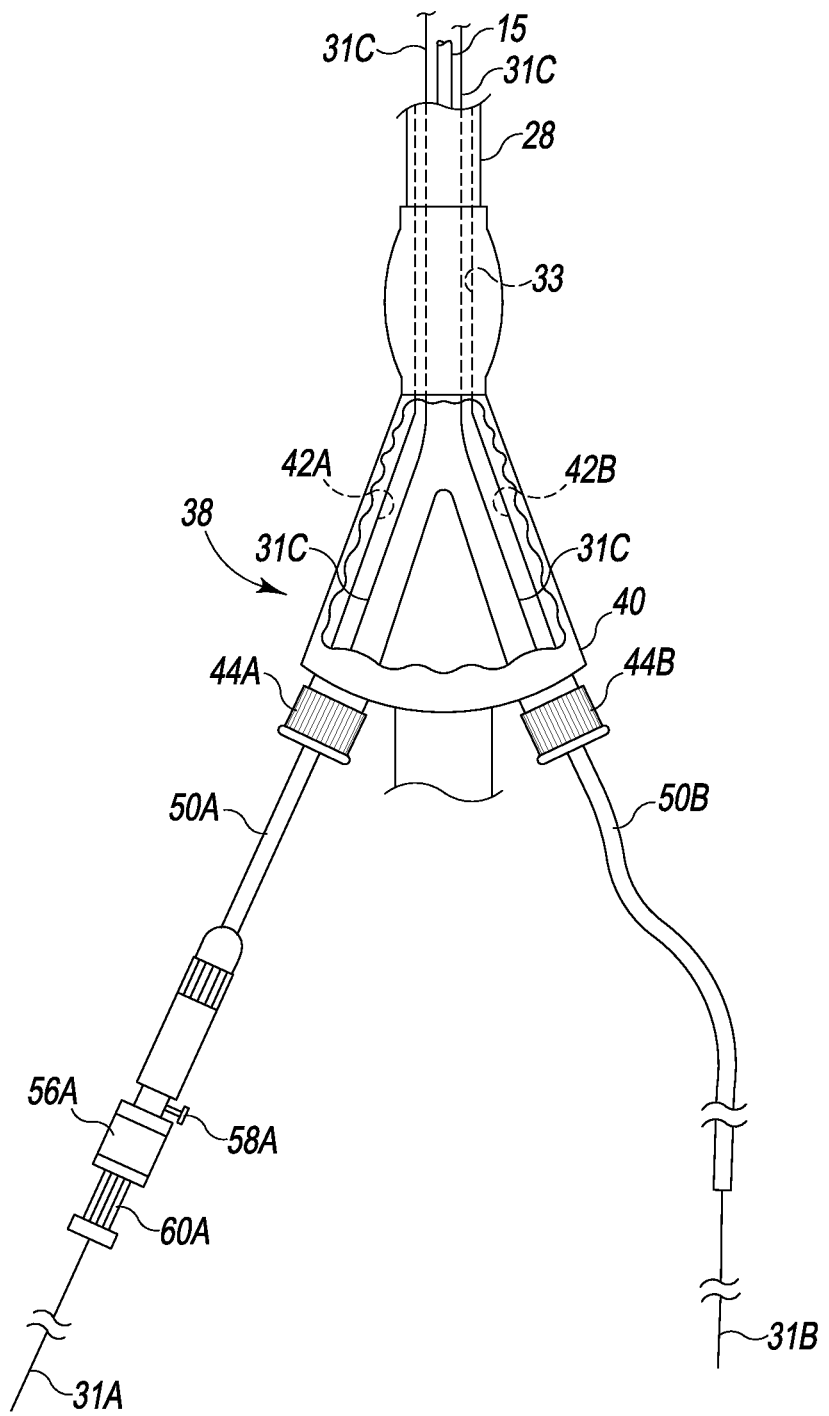
FIG. 3 depicts a proximal portion of a device for delivering and deploying a prosthesis, including a prosthesis with a precannulated fenestration.

FIG. 3 depicts an exemplary access device 38 with multiple channels 42A, 42B in communication with multiple ports 44A, 44B. The ports 44A, 44B may be used, for example, to introduce medical reagents to the prosthesis through the pusher 28. Alternatively or additionally, the ports 44A, 44B may be used to introduce auxiliary medical devices such as guide wires or interventional catheters to the prosthesis through the pusher 28.

The access device 38 preferably includes one or more haemostatic valves (not shown), as described above, to control blood loss during a procedure. For example, one or more ports 44A, 44B may comprise one or more disk valves, iris valves, or the like. Alternatively or additionally one or more such valves may be placed within channel 42 to control blood loss through the access device 38.

FIGS. 1-4 depict delivery and deployment devices comprising a prosthesis 20 with at least one precannulated fenestration 27. The devices comprise a wire 31 having a first end 31A, a second end 31B, and a body portion 31C disposed between the ends. The wire 31 may be formed from any suitable material, such as a biocompatible metal or plastic, and with dimensions suitable for the particular application. In one example, a wire comprises a highly elastic metal, such as nitinol or the like, and has a diameter in the range of about 0.016 to about 0.018 inches. Wires made of other materials, and having other diameters are also contemplated.

The wire 31 traverses the delivery catheter 1 between proximal and distal end portions of the catheter. Each wire end 31A, 31B is disposed at the external manipulation section 3 of the delivery catheter 1 and can be directly manipulated by the operator during a procedure. The wire 31 extends distally from the first end 31A through port 44A, through axial lumen 33 (shown, for example, in FIG. 3) of the delivery catheter, into the lumen of the prosthesis 20 (shown, for example, in FIG. 2), and through fenestration 27, 27A to the exterior of the graft 18 (shown, for example, in FIGS. 1 and 2). The wire 31 then extends proximally through the lumen of the prosthesis 20, through axial lumen 33 (shown, for example, in FIG. 3), and through port 44B towards the second wire end 31B.

In some examples, lumen 33 may comprise a single lumen structure and the wire 31 will extend proximally and distally along the delivery catheter through a single lumen structure. In other examples, lumen 33 may comprise a multi-lumen structure and the wire 31 will extend proximally and distally along the delivery catheter through separate lumen structures.

The wire 31 is slidably disposed within the fenestration 27, 27A. Consequently, the operator can move the wire 31 proximally through the fenestration 27, 27A by pulling proximally on the first wire end 31A or by pushing distally on the second wire end 31B. Similarly, the operator can move the wire 31 distally through the fenestration 27, 27A by pulling proximally on the second wire end 31B or by pushing distally on the first wire end 31A. This feature provides the operator with control over the positioning and configuration of the wire 31 with respect to the fenestration 27, 27A. For example, it may be possible to manipulate the angle of the wire 31 as it passes through the fenestration 27, 27A by fixing the position of the first wire end 31A and manipulating the second wire end 31B, or vice versa. Other advantages of this feature will be apparent to one of ordinary skill in the art.

Figure 2:
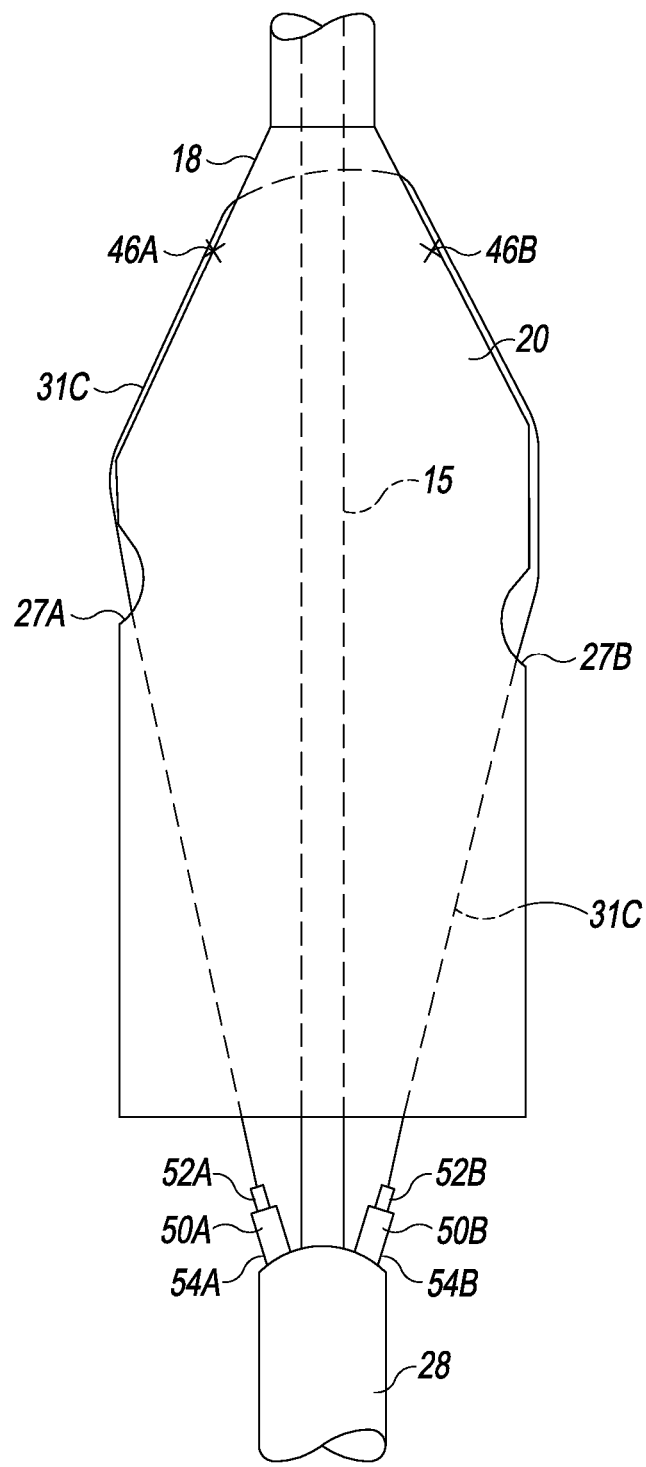
FIG. 2 depicts a distal portion of a device for delivering and deploying a prosthesis, including a prosthesis with a precannulated fenestration.

FIG. 2 depicts a prosthesis 20 with multiple (more than one) precannulated fenestrations 27A, 27B. Wire 31 extends distally from first wire end 31A through axial lumen 33 of the delivery catheter, into the lumen of the prosthesis 20, and through fenestration 27A to the exterior of the graft 18. The wire 31 extends proximally from the exterior of the graft 18 through fenestration 27B into the lumen of the prosthesis 20, and through axial lumen 33 towards the second wire end 31B. As shown in FIG. 2, one or more stabilizing sutures 46A, 46B may be provided along the prosthesis 20 to attach the wire 31 to the graft material and/or to the stent structure. Sutures 46A, 46B preferably limit lateral movement of the wire, but allow the wire to slide axially through the fenestrations 27A, 27B, as described above.

As shown in FIG. 2, the wire 31 may pass through the lumen of the prosthesis 20 as it traverses fenestrations 27A, 27B. In some examples, the wire extends approximately 3 cm or more away from a fenestration and then passes through the graft material into the lumen of the prosthesis. In other examples, the wire extends approximately 6 cm or less away from a fenestration and then passes through the graft material into the lumen of the prosthesis. In other examples, the wire 31 traverses fenestrations 27A, 27B without passing through the lumen of the prosthesis 20.

Figure 4:
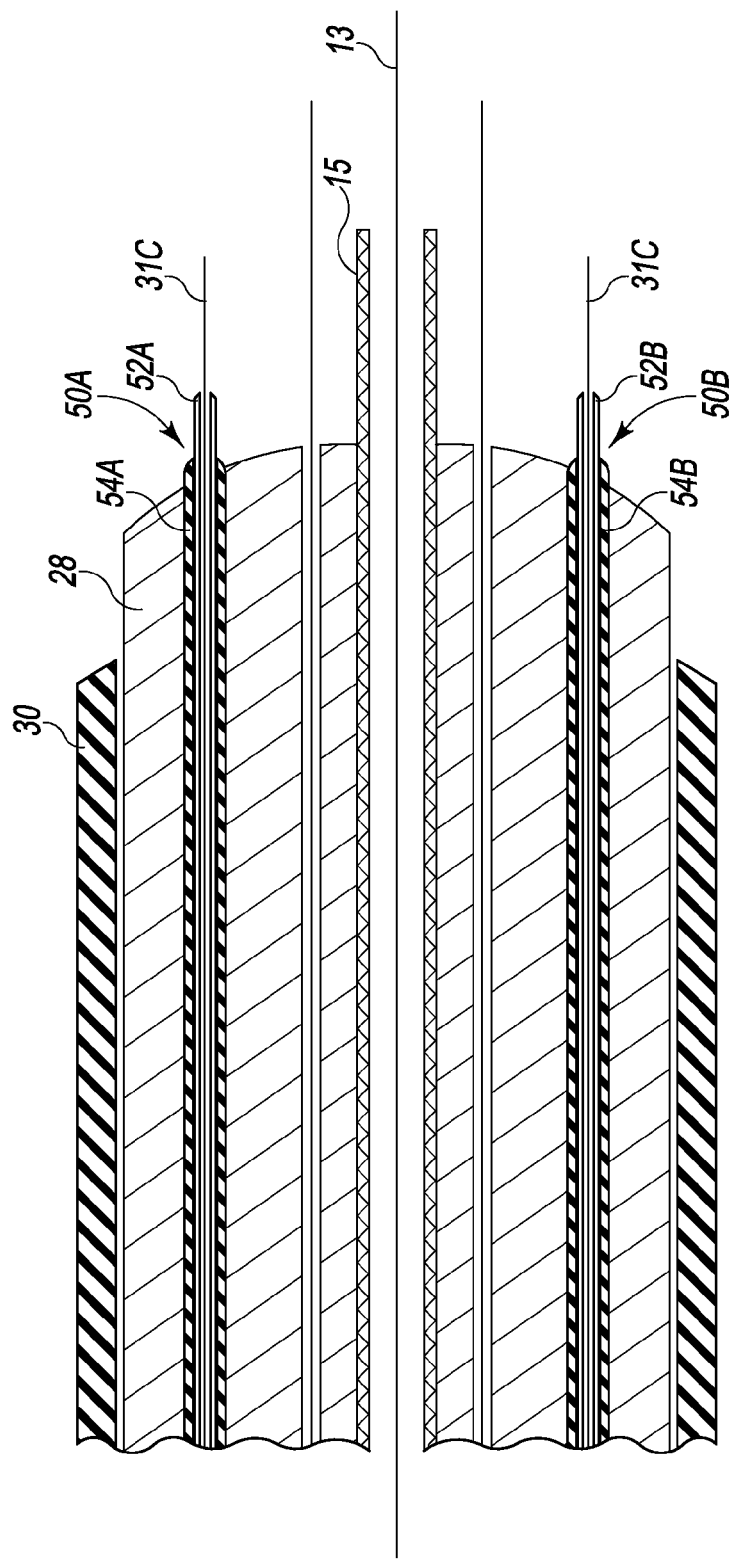
FIG. 4 is a cross-sectional view of a distal portion of a pusher comprising auxiliary catheters and a precannulating wire structure.

As shown in FIGS. 2-4, auxiliary catheters 50A, 50B may be provided and delivered to the prosthesis 20 through the auxiliary access device 38. Auxiliary catheters 50A, 50B may comprise, for example, an elongate sheath 54A, 54B, and an elongate dilator 52A, 52B slidably disposed within an axial lumen of the sheath 54A, 54B. Auxiliary catheters 50A, 50B may also comprise haemostatic sealing means 56A, 56B, as described above, to limit or prevent blood loss through the auxiliary catheters. In addition, catheters 50A, 50B may comprise side tubes 58A, 58B for introducing medical reagents through the auxiliary catheters. The dilators 52A, 52B terminate proximally at connection means 60A, 60B. Connection means 60A, 60B may be configured for introducing medical reagents through the auxiliary catheters. Auxiliary catheters 50A, 50B are delivered to the prosthesis over the wire ends 31A, 31B through the lumen 33 of the pusher 28, as described above.

Auxiliary catheters 50A, 50B may be used to deliver medical devices, such as guide wires, balloons, stents, stent grafts, imaging devices, and the like, from the user manipulation section 3 to the prosthesis 20. For example, as described in greater detail below, auxiliary catheters 50A, 50B may be used to cannulate target vessels through the fenestrations 27A, 27B.

Figure 5:
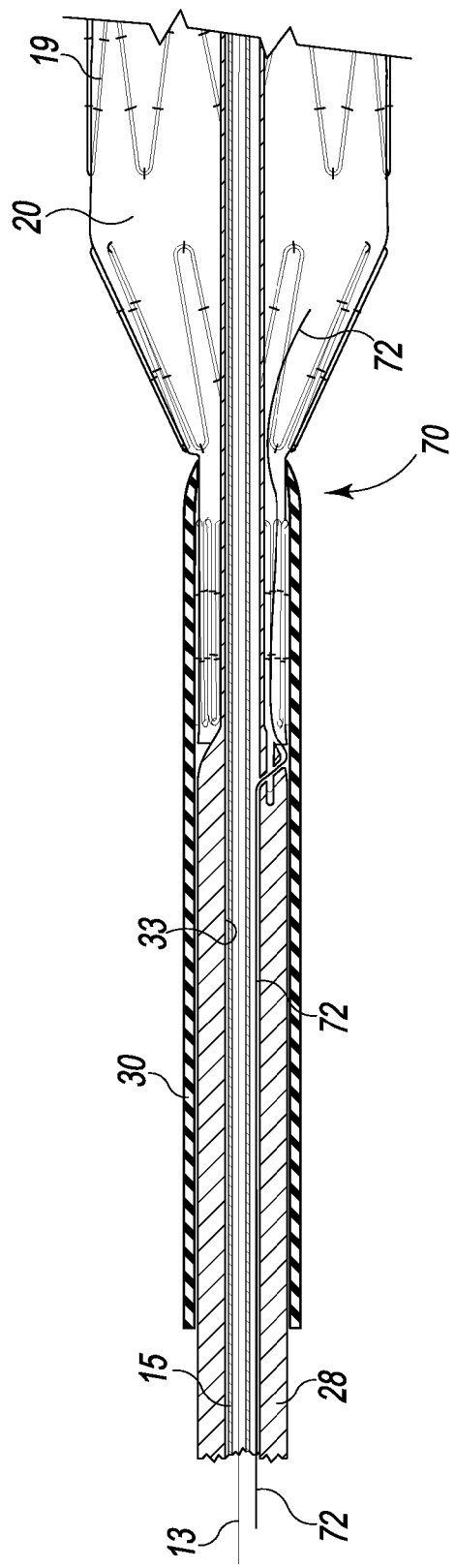
FIG. 5 is a cross-sectional view of a proximal attachment region for a delivery and deployment device.
Figure 6:
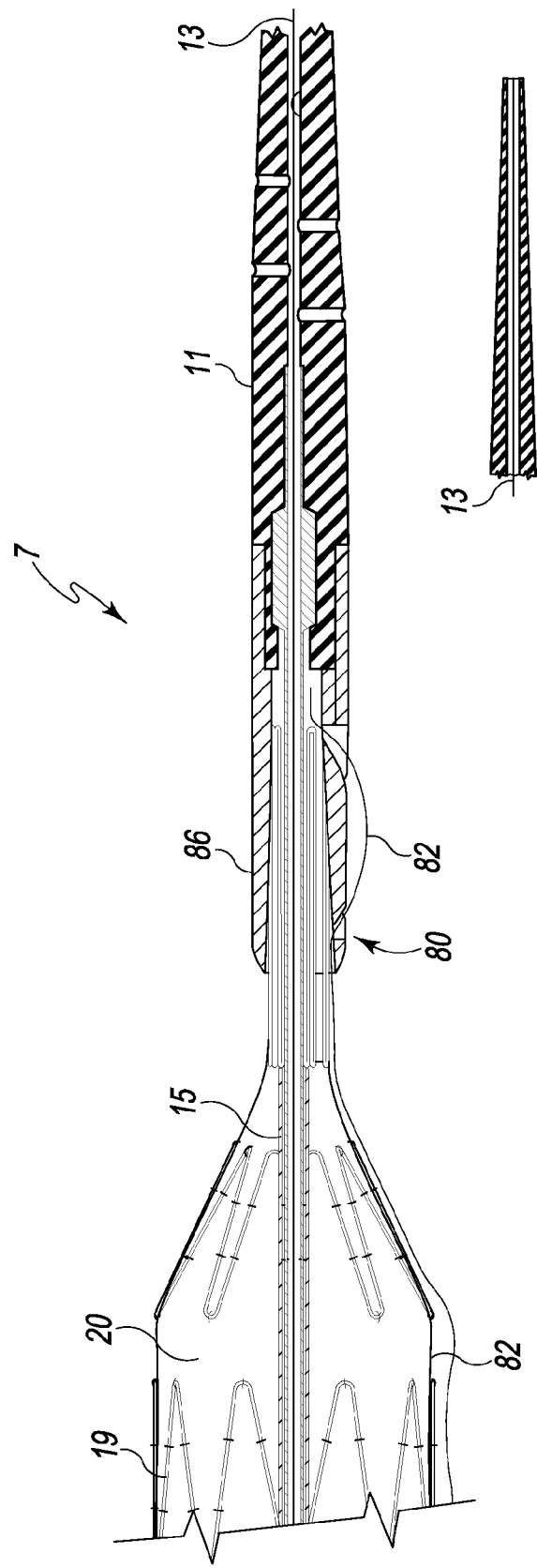
FIG. 6 is a cross-sectional view of a distal attachment region for a delivery and deployment device.

As shown in FIGS. 1, 5, and 6, a device for delivering and deploying a prosthesis may optionally comprise one or more retention devices for retaining at least a portion of the prosthesis. For example, a delivery catheter 1 may comprise a proximal prosthesis retention device 70 for retaining a proximal end of the prosthesis 20, and a distal prosthesis retention device 80 for retaining a distal end of the prosthesis. FIGS. 1 and 5 depict an exemplary proximal prosthesis retention device 70 comprising a proximal trigger wire 72. Trigger wire 72 extends between the prosthesis 20 and the external manipulation section 3 through an axial lumen 33 of the pusher 28. Trigger wire 72 is preferably disposed in an axial lumen separate from the cannulating wire 31 to prevent entanglement between the wires. A proximal end of wire 72 is connected to control member 74 (FIG. 1). A distal end of the wire 72 is removably connected to the proximal end of the prosthesis 20 (FIG. 5) and limits axial displacement of the prosthesis. The trigger wire 72 can be disconnected from the proximal end of the prosthesis 20 by manipulating the control member 74, for example by sliding the control member proximally to pull the wire away from the prosthesis. Clamping screw 75 may be provided to clamp the control member 74 to prevent inadvertent disengagement of the trigger wire 72.

FIGS. 1 and 6 depict an exemplary distal prosthesis retention device 80 comprising a distal trigger wire 82 and top cap 86. The cap 86 is fixedly coupled to the inner cannula 15 and holds the distal end of the prosthesis 20 in a radially constrained configuration. The cap 86 prevents the distal end of the prosthesis 20 from expanding during use. Trigger wire 82 extends between the prosthesis 20 and the external manipulation section 3 through an axial lumen 33 of the pusher 28. Trigger wire 82 is preferably disposed in an axial lumen separate from the cannulating wire 31 to prevent entanglement of the wires. A proximal end of wire 82 is connected to control member 84 (FIG. 1). A distal end of the wire 82 is removably connected to the distal end of the prosthesis 20 and to the cap 86. The trigger wire 82 can be disconnected from the prosthesis 20 and cap 86 by manipulating the control member 84, for example by sliding the control member proximally to pull the wire away from the prosthesis and the cap. Clamping screw 85 may be provided to clamp the control member 84 to prevent inadvertent disengagement of the trigger wire 82. Once the wire 82 disengages the prosthesis 20 and cap 86, the cap can be removed from the prosthesis by sliding the inner cannula 15 distally with respect to the pusher 28.

Various devices and systems for retaining proximal, distal, and medial portions of a prosthesis are disclosed in the patent literature, For example U.S. Pat. Nos. 6,524,335, 7,335,224, 7,435,253, 7,537,606, 7,611,529, 7,651,519, and 7,722,657, and U.S. Published Patent Application Nos. 2004/230287 A1, 2006/0004433 A1, 2007/0043425 A1, and 2008/0294234 A1 disclose devices and systems that are suitable for use with the present invention. Each of these patent references is incorporated herein by reference in its entirety.

FIGS. 7-12 depict various stages of a method for delivering and deploying a prosthesis comprising a precannulated fenestration into the aorta. Although the method is described in relation to a device for treating the aorta, it can readily be applied to other devices and indications.

A delivery catheter 1, as described for example with respect to FIG. 1, is provided and comprises a pusher 28 and an inner cannula 15 slidingly disposed within an axial lumen of the pusher. The delivery catheter 1 is slidingly disposed within an axial lumen of sheath 30. Prosthesis 20 is disposed over a distal end portion of the delivery catheter 1 within the axial lumen of sheath 30. A top cap 86 retains a distal end portion of the prosthesis 20 to prevent premature radial expansion of the distal end of the prosthesis as the sheath 30 is retracted proximally over the delivery catheter 1. Although not shown in FIGS. 7-12, the prosthesis 20 may comprise one or more expandable stents, as described above.

Figure 7:
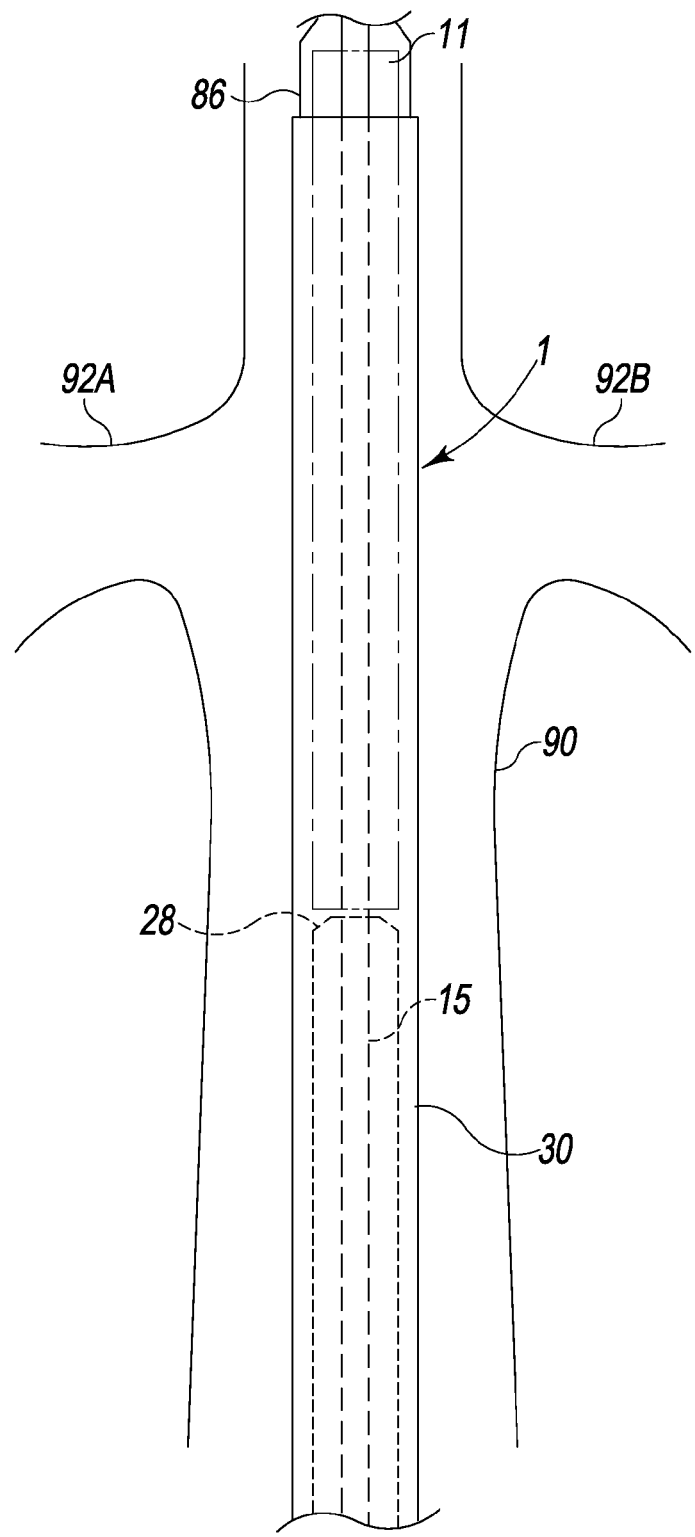
FIGS. 7-12 depict various stages of a method of using a delivery and deployment device including a prosthesis with precannulated fenestrations.

FIG. 7 depicts the delivery and deployment device disposed in an undeployed configuration within a vessel 90 (such as the aorta). The device comprises a prosthesis 20 with multiple fenestrations 27A, 27B sized and configured to provide fluid communication between the lumen of the prosthesis 20 and the branch vessels 92A, 92B (such as renal arteries) after the prosthesis is deployed. Consequently, the prosthesis 20 can be placed within vessel 90 so that it overlaps branch vessels 92A, 92B without occluding the branch vessels. The prosthesis comprises precannulated fenestrations 27A, 27B, as described above. In particular, a wire 31 is provided having a first end 31A, a second end 31B, and a wire body 31C. Wire 31 extends distally from first wire end 31A through axial lumen 33 of the delivery catheter, into the lumen of the prosthesis 20, and through fenestration 27A to the exterior of the graft 18. The wire 31 extends proximally from the exterior of the graft 18 through fenestration 27B into the lumen of the prosthesis 20, and through axial lumen 33 towards the second wire end 31B.

The delivery catheter 1 may be delivered within the vessel 90 in a conventional manner. A guide wire (not shown) is introduced, for example, into a femoral artery and advanced into the vessel until the tip of the guide wire extends beyond the region in which the prosthesis 20 will be placed. The delivery and deployment device is then inserted over the guide wire 13, via inner cannula 15, into the vessel 90 and positioned by radiographic techniques generally known in the art. Provision may be made for a separate angiographic catheter (not shown) at the level of the branch vessels 92.

At this stage, the prosthesis 20 is disposed in a compressed configuration within the top cap 86 and an axial lumen of the sheath 30. An auxiliary catheter 50A may be provided and inserted over the first wire end 31A and through port 44A into an axial lumen of the delivery catheter 1. Likewise, an auxiliary catheter 50B may be provided and inserted over the second wire end 31B and through port 44B into an axial lumen of the delivery catheter 1.

Figure 8:
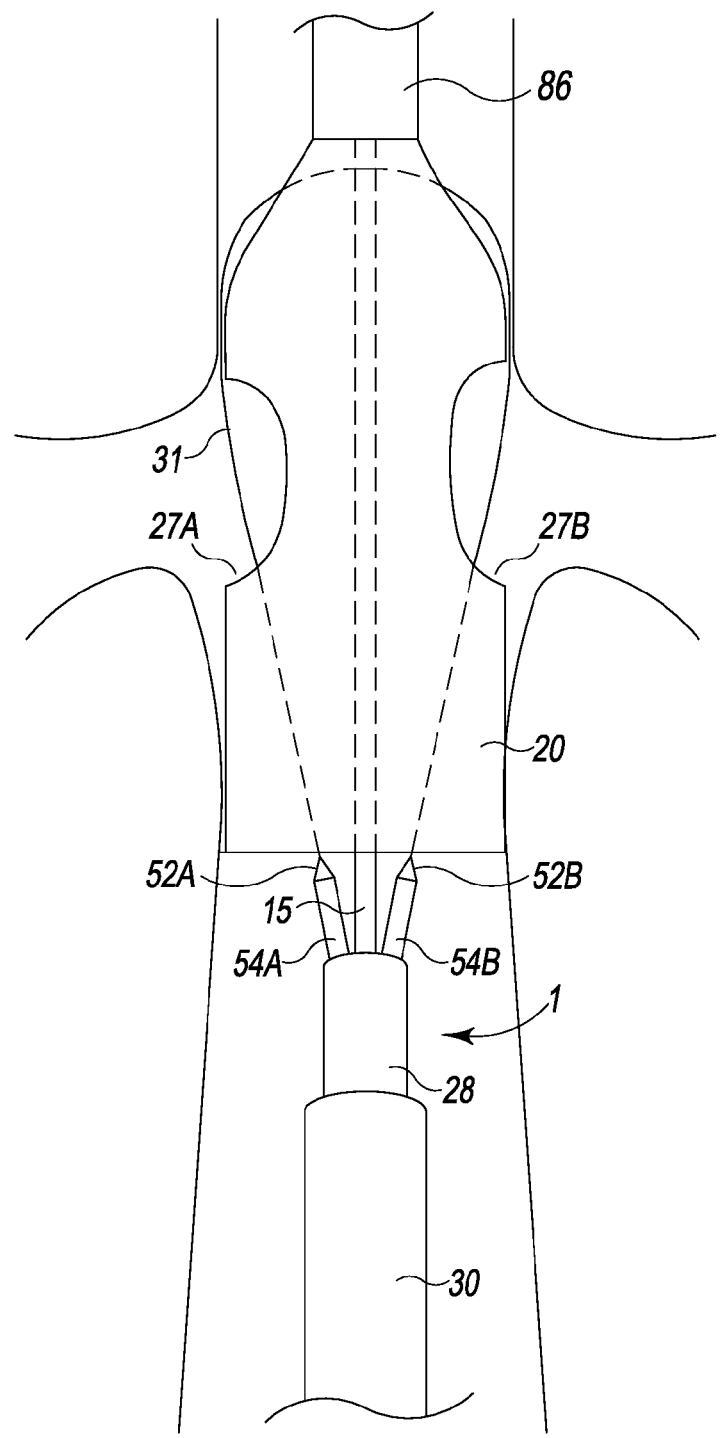

The delivery and deployment device is positioned within the vessel by radiographic means so that the prosthesis 20 overlaps the ostia of, and fenestrations 27A, 27B align with, the branch vessels 92A, 92B. Once the device is in a proper position, the sheath 30 is retracted to expose the prosthesis 20. This action releases the prosthesis so that it can expand radially towards the vessel walls, as shown in FIG. 8. The top cap 86 retains the distal end of the prosthesis 20, however, and prevents it from expanding at this stage. The operator may release the distal end of the prosthesis 20 at a desired stage by sliding the top cap 86 distally with respect to the prosthesis.

Figure 9:
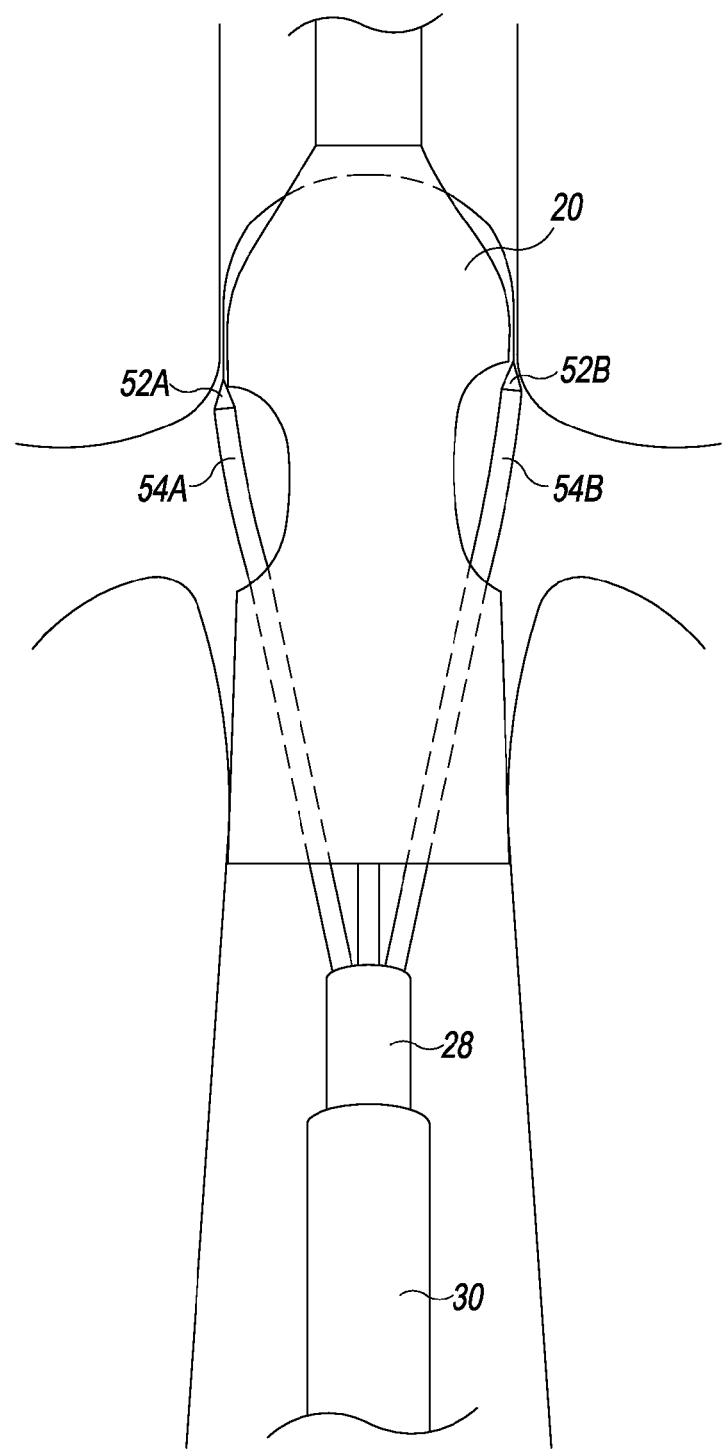
Figure 10:
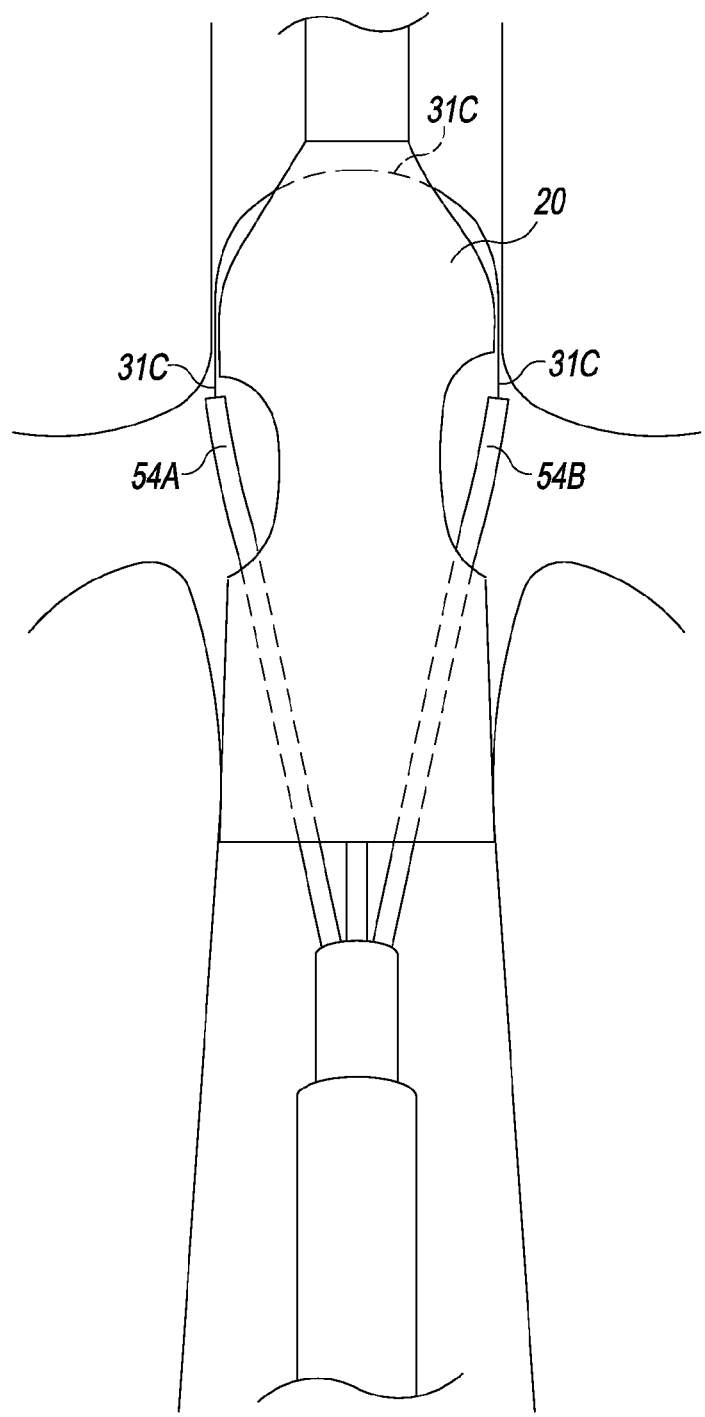

In FIG. 9, auxiliary catheter 50A is advanced distally over the wire 31 within the lumen of the prosthesis 20 until the distal end of sheath 54A passes through fenestration 27A. Similarly, auxiliary catheter 50B is advanced distally over the wire 31 within the lumen of the prosthesis 20 until the distal end of sheath 54B passes through fenestration 27B. In FIG. 10, dilators 52A, 52B of the auxiliary catheters 50A, 50B have been removed by withdrawing them proximally through the sheaths 54A, 54B.

Figure 11:
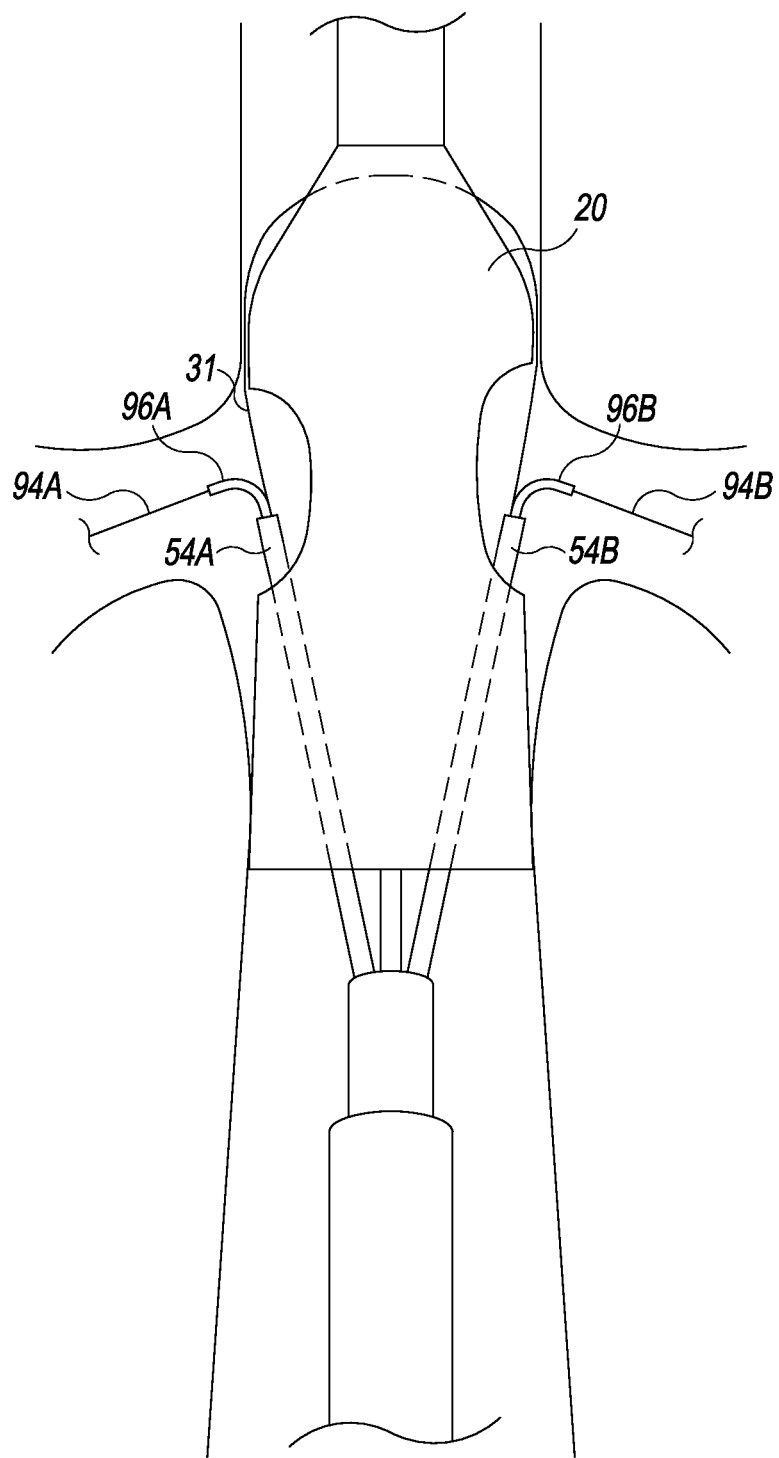

Next, branch guide wires 94A, 94B are provided for cannulating the branch vessels. As shown in FIG. 11, branch guide wire 94A is delivered through sheath 54A alongside a first end portion of wire 31 and branch guide wire 94B is delivered through sheath 54B alongside a second end portion of wire 31. Branch access catheters 96A, 96B are then introduced over guide wires 94A, 94B, respectively. Access catheters 96A, 96B preferably have steerable distal end portions that can be used to guide the branch wires 94A, 94B through the fenestrations 27A, 27B and into respective branch vessels 92A, 92B. Suitable catheters are commercially available and include the Torcon NB® Advantage Catheters available from Cook, Inc., Bloomington Ind., USA.

Once the branch vessels are cannulated, catheters 96A, 96B are removed, by withdrawing them proximally through sheaths 54A, 54B. At this point, the preloaded wire 31 is no longer needed and may be removed by pulling proximally on the first wire end 31A until the second wire end 31B exits port 44A, or by pulling on the second wire end until the first wire end exits port 44B.

Figure 12:
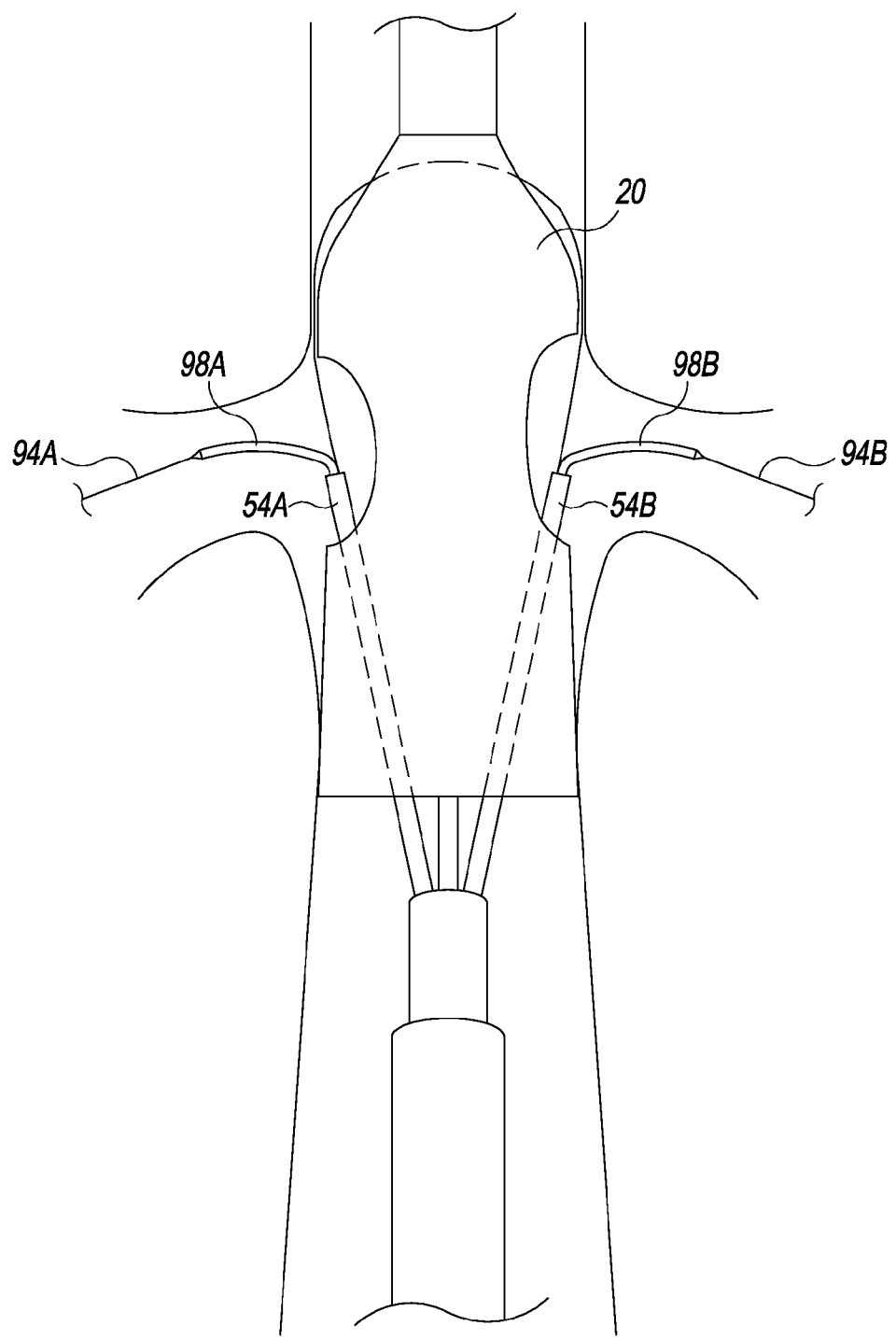

With guide wires 94A, 94B in place, the operator may now deliver one or more interventional catheters 98A, 98B (including, for example, catheters carrying balloons, stents, grafts, imaging devices, and the like) into the branch vessels 92A, 92B through fenestrations 27A, 27B, as shown in FIG. 12.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together.

The invention claimed is:

1. A device for delivering and deploying an endoluminal prosthesis, the device comprising:
    a delivery catheter having at least one axial lumen; and
    an endoluminal prosthesis disposed at a distal end portion of the delivery catheter and comprising a tubular graft having a first opening at a first end, a second opening at a second end, and at least one fenestration in the graft between the first and second ends; and
    a wire comprising first and second ends, each disposed at a proximal end portion of the delivery catheter, and a body portion disposed between the first and second ends of the wire; where the wire extends distally from the first wire end through an axial lumen of the delivery catheter and the prosthesis, and through the fenestration in the graft; and
    where the wire extends proximally through a lumen of the prosthesis and through an axial lumen of the delivery catheter towards the second wire end.

2. The device of claim 1, further comprising an auxiliary catheter slid ably disposed within an axial lumen of the delivery catheter over a first end portion of the wire.

3. The device of claim 2, where the auxiliary catheter comprises an elongate sheath and an elongate dilator disposed within an axial lumen of the sheath.

4. The device of claim 2, further comprising a second auxiliary catheter slidably disposed within an axial lumen of the delivery catheter over a second end portion of the wire.

5. The device of claim 4, where the second auxiliary catheter comprises an elongate sheath and an elongate dilator disposed within an axial lumen of the sheath.

6. The device of claim 1, where the prosthesis comprises two or more fenestrations in the graft.

7. The device of claim 1 comprising one or more attachment points between the prosthesis and the wire.

8. The device of claim 7, where each of the attachment points comprises a suture.

9. The device of claim 7, where the one or more attachment points attach the wire to an exterior surface of the prosthesis.

10. The device of claim 7, where the wire is slid ably disposed through the fenestration.

11. The device of claim 1, where the wire is slid ably disposed through the fenestration.

12. The device of claim 1, further comprising any two or more of the following:
    an auxiliary catheter slidably disposed within an axial lumen of the delivery catheter over a first end portion of the wire;
    the auxiliary catheter comprises an elongate sheath and an elongate dilator disposed within an axial lumen of the sheath;
    a second auxiliary catheter slidably disposed within an axial lumen of the delivery catheter over a second end portion of the wire;
    the second auxiliary catheter comprises an elongate sheath and an elongate dilator disposed within an axial lumen of the sheath;
    the prosthesis comprises two or more fenestrations in the graft;
    one or more attachment points between the prosthesis and the wire;
    each of the attachment points comprises a suture;
    the one or more attachment points attach the wire to an exterior surface of the prosthesis; and
    the wire is slidably disposed through the fenestration.

\* \* \* \* \*